United States Patent
Crow et al.

(10) Patent No.: US 7,291,158 B2
(45) Date of Patent: Nov. 6, 2007

(54) CUTTING BALLOON CATHETER HAVING A SEGMENTED BLADE

(75) Inventors: Loren M. Crow, Las Mesa, CA (US); Steven W. Bence, Vista, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 322 days.

(21) Appl. No.: 10/987,011

(22) Filed: Nov. 12, 2004

(65) Prior Publication Data

US 2006/0106412 A1    May 18, 2006

(51) Int. Cl.
*A61B 17/22* (2006.01)
*A61B 17/32* (2006.01)
*A61M 29/00* (2006.01)

(52) U.S. Cl. ............... 606/159; 606/167; 606/170; 606/191; 606/192; 606/194

(58) Field of Classification Search ............... 606/159, 606/167, 170, 191, 192, 194
See application file for complete search history.

(56) References Cited

U.S. PATENT DOCUMENTS

| | | | |
|---|---|---|---|
| 2,816,552 A | 12/1957 | Hoffman |
| 3,174,851 A | 3/1965 | Buehler et al. |
| 3,351,463 A | 11/1967 | Rozner et al. |
| 3,635,223 A | 1/1972 | Klieman |
| 3,749,085 A | 7/1973 | Willson et al. |
| 3,753,700 A | 8/1973 | Harrison et al. |
| 3,990,453 A | 11/1976 | Douvas et al. |
| 4,140,126 A | 2/1979 | Choudhury |
| 4,141,364 A | 2/1979 | Schultze |
| 4,263,236 A | 4/1981 | Briggs et al. |
| 4,273,128 A | 6/1981 | Lary |
| 4,292,974 A | 10/1981 | Fogarty et al. |
| 4,406,656 A | 9/1983 | Hattler et al. |
| 4,465,072 A | 8/1984 | Taheri |
| 4,490,421 A | 12/1984 | Levy |
| 4,572,186 A | 2/1986 | Gould et al. |
| 4,574,781 A | 3/1986 | Chin |

(Continued)

FOREIGN PATENT DOCUMENTS

DE      34 00 416 A1    7/1985

(Continued)

OTHER PUBLICATIONS

Lary, Banning G., et al., "A Method for Creating a Coronary-Myocardial Artery," *Surgery*, Jun. 1966, vol. 59. No. 6, pp. 1061-1064.

(Continued)

*Primary Examiner*—(Jackie) Tan-Uyen Ho
*Assistant Examiner*—Amanda Adams
(74) *Attorney, Agent, or Firm*—Crompton, Seager & Tufte, LLC

(57) ABSTRACT

A cutting balloon catheter and method of making and using the same. The cutting balloon catheter may include a catheter shaft having a balloon coupled thereto. One or more cutting members or blades may be coupled to the balloon. The cutting members may include two or more sections that are connected via a fracturable or yielding bridge section that increases flexibility when passing through or being utilized in tortuous anatomy.

6 Claims, 11 Drawing Sheets

U.S. PATENT DOCUMENTS

| | | |
|---|---|---|
| 4,608,984 A | 9/1986 | Fogarty |
| 4,627,436 A | 12/1986 | Leckrone |
| 4,669,469 A | 6/1987 | Gifford, III et al. |
| 4,685,458 A | 8/1987 | Leckrone |
| 4,686,982 A | 8/1987 | Nash |
| 4,696,667 A | 9/1987 | Masch |
| 4,705,517 A | 11/1987 | DiPisa, Jr. |
| 4,723,549 A | 2/1988 | Wholey et al. |
| 4,728,319 A | 3/1988 | Masch |
| 4,747,405 A | 5/1988 | Leckrone |
| 4,748,982 A | 6/1988 | Horzewski et al. |
| 4,781,186 A | 11/1988 | Simpson et al. |
| 4,784,636 A | 11/1988 | Rydell |
| 4,787,388 A | 11/1988 | Hofmann |
| 4,790,813 A | 12/1988 | Kensey |
| 4,793,348 A | 12/1988 | Palmaz |
| 4,796,629 A | 1/1989 | Grayzel |
| 4,799,479 A | 1/1989 | Spears |
| RE32,983 E | 7/1989 | Levy |
| 4,867,157 A | 9/1989 | McGurk-Burleson et al. |
| 4,886,061 A | 12/1989 | Fischell et al. |
| 4,887,613 A | 12/1989 | Farr et al. |
| 4,896,669 A | 1/1990 | Bhate et al. |
| 4,909,781 A | 3/1990 | Husted |
| 4,921,483 A | 5/1990 | Wijay et al. |
| 4,921,484 A | 5/1990 | Hillstead |
| 4,936,845 A | 6/1990 | Stevens |
| 4,960,410 A | 10/1990 | Pinchuk |
| 4,963,313 A | 10/1990 | Noddin et al. |
| 4,966,604 A | 10/1990 | Reiss |
| 4,979,951 A | 12/1990 | Simpson |
| 4,986,807 A | 1/1991 | Farr |
| 4,994,018 A | 2/1991 | Saper |
| RE33,561 E | 3/1991 | Levy |
| 5,009,659 A | 4/1991 | Hamlin et al. |
| 5,015,231 A | 5/1991 | Keith et al. |
| 5,030,201 A | 7/1991 | Palestrant |
| 5,041,125 A | 8/1991 | Montano, Jr. |
| 5,042,985 A | 8/1991 | Elliott et al. |
| 5,047,040 A | 9/1991 | Simpson et al. |
| 5,053,007 A | 10/1991 | Euteneuer |
| 5,053,044 A | 10/1991 | Mueller et al. |
| 5,071,424 A | 12/1991 | Reger |
| 5,074,841 A | 12/1991 | Ademovic et al. |
| 5,074,871 A | 12/1991 | Groshong |
| 5,078,722 A | 1/1992 | Stevens |
| 5,078,725 A | 1/1992 | Enderle et al. |
| 5,084,010 A | 1/1992 | Plaia et al. |
| 5,085,662 A | 2/1992 | Willard |
| 5,087,246 A | 2/1992 | Smith |
| 5,087,265 A | 2/1992 | Summers |
| 5,100,424 A | 3/1992 | Jang et al. |
| 5,100,425 A | 3/1992 | Fischell et al. |
| 5,102,390 A | 4/1992 | Crittenden et al. |
| 5,102,403 A | 4/1992 | Alt |
| 5,116,318 A | 5/1992 | Hillstead |
| 5,135,482 A | 8/1992 | Neracher |
| 5,147,302 A | 9/1992 | Euteneuer et al. |
| 5,152,773 A | 10/1992 | Redha |
| 5,156,594 A | 10/1992 | Keith |
| 5,156,610 A | 10/1992 | Reger |
| 5,158,564 A | 10/1992 | Schnepp-Pesch et al. |
| 5,176,693 A | 1/1993 | Pannek, Jr. |
| 5,178,625 A | 1/1993 | Groshong |
| 5,180,368 A | 1/1993 | Garrison |
| 5,181,920 A | 1/1993 | Mueller et al. |
| 5,192,291 A | 3/1993 | Pannek, Jr. |
| 5,196,024 A | 3/1993 | Barath |
| 5,196,025 A | 3/1993 | Ranalletta et al. |
| 5,209,749 A | 5/1993 | Buelna |
| 5,209,799 A | 5/1993 | Vigil |
| 5,224,945 A | 7/1993 | Pannek, Jr. |
| 5,226,430 A | 7/1993 | Spears et al. |
| 5,226,887 A | 7/1993 | Farr et al. |
| 5,226,909 A | 7/1993 | Evans et al. |
| 5,234,450 A | 8/1993 | Segalowitz |
| 5,242,396 A | 9/1993 | Evard |
| 5,248,311 A | 9/1993 | Black et al. |
| 5,250,059 A | 10/1993 | Andreas et al. |
| 5,295,959 A | 3/1994 | Gurbel et al. |
| 5,300,025 A | 4/1994 | Wantink |
| 5,312,425 A | 5/1994 | Evans et al. |
| 5,318,576 A | 6/1994 | Plassche, Jr. et al. |
| 5,320,634 A | 6/1994 | Vigil et al. |
| 5,328,472 A | 7/1994 | Steinke et al. |
| 5,336,234 A | 8/1994 | Vigil et al. |
| 5,342,301 A | 8/1994 | Saab |
| 5,342,307 A | 8/1994 | Euteneuer et al. |
| 5,346,505 A | 9/1994 | Leopold |
| 5,350,361 A | 9/1994 | Tsukashima et al. |
| 5,372,601 A | 12/1994 | Lary |
| 5,395,361 A | 3/1995 | Fox et al. |
| 5,399,164 A | 3/1995 | Snoke et al. |
| 5,403,334 A | 4/1995 | Evans et al. |
| 5,409,454 A | 4/1995 | Fischell et al. |
| 5,411,466 A | 5/1995 | Hess |
| 5,411,478 A | 5/1995 | Stillabower |
| 5,415,654 A | 5/1995 | Daikuzono |
| 5,417,653 A | 5/1995 | Sahota et al. |
| 5,417,703 A | 5/1995 | Brown et al. |
| 5,423,745 A | 6/1995 | Todd et al. |
| 5,425,711 A | 6/1995 | Ressemann et al. |
| 5,425,712 A | 6/1995 | Goodin |
| 5,437,659 A | 8/1995 | Leckrone |
| 5,441,510 A | 8/1995 | Simpson et al. |
| 5,449,343 A | 9/1995 | Samson et al. |
| 5,456,666 A | 10/1995 | Campbell et al. |
| 5,456,681 A | 10/1995 | Hajjar |
| 5,458,572 A | 10/1995 | Campbell et al. |
| 5,478,319 A | 12/1995 | Campbell et al. |
| 5,487,730 A | 1/1996 | Marcadis et al. |
| 5,496,308 A | 3/1996 | Brown et al. |
| 5,507,760 A * | 4/1996 | Wynne et al. ............... 606/159 |
| 5,507,761 A | 4/1996 | Duer |
| 5,522,818 A | 6/1996 | Keith et al. |
| 5,522,825 A | 6/1996 | Kropf et al. |
| 5,538,510 A | 7/1996 | Fontirroche et al. |
| 5,542,924 A | 8/1996 | Snoke et al. |
| 5,549,556 A | 8/1996 | Ndondo-Lay et al. |
| 5,554,121 A | 9/1996 | Ainsworth et al. |
| 5,556,405 A | 9/1996 | Lary |
| 5,556,408 A | 9/1996 | Farhat |
| 5,569,277 A | 10/1996 | Evans et al. |
| 5,571,087 A | 11/1996 | Ressemann et al. |
| 5,616,149 A | 4/1997 | Barath |
| 5,628,761 A | 5/1997 | Rizik |
| 5,643,209 A | 7/1997 | Fugoso et al. |
| 5,643,296 A | 7/1997 | Hundertmark et al. |
| 5,649,941 A | 7/1997 | Lary |
| 5,662,671 A | 9/1997 | Barbut et al. |
| 5,669,920 A | 9/1997 | Conley et al. |
| 5,681,336 A | 10/1997 | Clement et al. |
| 5,697,944 A | 12/1997 | Lary |
| 5,713,913 A | 2/1998 | Lary et al. |
| 5,718,684 A | 2/1998 | Gupta |
| 5,720,724 A | 2/1998 | Ressemann et al. |
| 5,728,123 A | 3/1998 | Lemelson et al. |
| 5,743,875 A | 4/1998 | Sirhan et al. |
| 5,759,191 A | 6/1998 | Barbere |
| 5,769,819 A | 6/1998 | Schwab et al. |
| 5,769,865 A | 6/1998 | Kermode et al. |
| 5,792,158 A | 8/1998 | Lary |
| 5,797,935 A | 8/1998 | Barath |
| 5,800,450 A | 9/1998 | Lary et al. |

| | | |
|---|---|---|
| 5,820,594 A | 10/1998 | Fontirroche et al. |
| 5,824,173 A | 10/1998 | Fontirroche et al. |
| 5,827,201 A | 10/1998 | Samson et al. |
| 5,827,225 A | 10/1998 | Ma Schwab |
| 5,827,310 A | 10/1998 | Mann et al. |
| 5,895,402 A | 4/1999 | Hundertmark et al. |
| 5,921,958 A | 7/1999 | Ressemann et al. |
| 5,931,819 A | 8/1999 | Fariabi |
| 5,993,469 A | 11/1999 | Barbut et al. |
| 5,997,557 A | 12/1999 | Barbut et al. |
| 6,010,521 A | 1/2000 | Lee et al. |
| 6,024,722 A | 2/2000 | Rau et al. |
| 6,030,371 A | 2/2000 | Pursley |
| 6,039,699 A | 3/2000 | Viera |
| 6,048,350 A | 4/2000 | Vrba |
| 6,066,149 A | 5/2000 | Samson et al. |
| 6,068,623 A | 5/2000 | Zadno-Azizi et al. |
| 6,110,192 A | 8/2000 | Ravenscroft et al. |
| 6,117,153 A | 9/2000 | Lary et al. |
| 6,139,510 A | 10/2000 | Palermo |
| 6,142,975 A | 11/2000 | Jalisi et al. |
| 6,165,140 A | 12/2000 | Ferrera |
| 6,165,167 A | 12/2000 | Delaloye |
| 6,165,292 A | 12/2000 | Abrams et al. |
| 6,168,571 B1 | 1/2001 | Solar et al. |
| 6,179,851 B1 | 1/2001 | Barbut et al. |
| 6,190,332 B1 | 2/2001 | Muni et al. |
| 6,193,686 B1 | 2/2001 | Estrada et al. |
| 6,213,957 B1 | 4/2001 | Milliman et al. |
| 6,217,549 B1 | 4/2001 | Selmon et al. |
| 6,217,567 B1 | 4/2001 | Zadno-Azizi et al. |
| 6,221,006 B1 | 4/2001 | Dubrul et al. |
| 6,241,690 B1 | 6/2001 | Burkett et al. |
| 6,254,550 B1 | 7/2001 | McNamara et al. |
| 6,258,108 B1 | 7/2001 | Lary |
| 6,283,743 B1 | 9/2001 | Traxler et al. |
| 6,306,105 B1 | 10/2001 | Rooney et al. |
| 6,306,151 B1 | 10/2001 | Lary |
| 6,309,399 B1 | 10/2001 | Barbut et al. |
| 6,319,242 B1 | 11/2001 | Patterson et al. |
| 6,344,029 B1 | 2/2002 | Estrada et al. |
| 6,355,016 B1 | 3/2002 | Bagaoisan et al. |
| 6,383,146 B1 | 5/2002 | Klint |
| 6,387,075 B1 | 5/2002 | Stivland et al. |
| 6,394,995 B1 | 5/2002 | Solar et al. |
| 6,398,798 B2 | 6/2002 | Selmon et al. |
| 6,409,863 B1 | 6/2002 | Williams et al. |
| 6,425,882 B1 | 7/2002 | Vigil |
| 6,428,552 B1 | 8/2002 | Sparks |
| 6,471,673 B1 | 10/2002 | Kasterhofer |
| 6,471,713 B1 | 10/2002 | Vargas et al. |
| 6,533,754 B1 | 3/2003 | Hisamatsu et al. |
| 6,544,276 B1 | 4/2003 | Azizi |
| 6,562,062 B2 * | 5/2003 | Jenusaitis et al. .......... 623/1.11 |
| 6,565,527 B1 | 5/2003 | Jonkman et al. |
| 6,602,265 B2 | 8/2003 | Dubrul et al. |
| 6,632,231 B2 | 10/2003 | Radisch, Jr. |
| 6,730,105 B2 | 5/2004 | Shiber |
| 6,746,463 B1 * | 6/2004 | Schwartz .................... 606/159 |
| 2002/0010489 A1 * | 1/2002 | Grayzel et al. ............. 606/194 |
| 2002/0082592 A1 | 6/2002 | Lary |
| 2003/0040770 A1 | 2/2003 | Radisch, Jr. |
| 2003/0144677 A1 | 7/2003 | Lary |
| 2003/0163148 A1 | 8/2003 | Wang et al. |
| 2004/0098014 A1 | 5/2004 | Flugelman et al. |
| 2004/0098018 A1 | 5/2004 | Radisch, Jr. |
| 2004/0122457 A1 | 6/2004 | Weber |
| 2004/0127920 A1 | 7/2004 | Radisch, Jr. |
| 2004/0133223 A1 | 7/2004 | Weber |
| 2004/0138733 A1 * | 7/2004 | Weber et al. ............... 623/1.11 |
| 2004/0230178 A1 | 11/2004 | Wu |
| 2004/0243156 A1 | 12/2004 | Wu et al. |

FOREIGN PATENT DOCUMENTS

| | | |
|---|---|---|
| DE | 34 02 573 A1 | 8/1985 |
| DE | 35 19 626 A1 | 12/1986 |
| EP | 0 291 170 A1 | 11/1988 |
| EP | 0 414 350 A1 | 2/1991 |
| EP | 0 565 796 A1 | 10/1993 |
| EP | 0 784 966 B1 | 7/1997 |
| EP | 0 792 656 A1 | 9/1997 |
| GB | 1 547 328 | 6/1979 |
| WO | WO 90/07909 A1 | 7/1990 |
| WO | WO 91/17714 A1 | 11/1991 |

OTHER PUBLICATIONS

Lary, Banning G., "A Method to Create and Correct Stenosis of a Coronary Artery," *Archives of Surgery*, Nov. 1966, vol. 93, pp. 828-830.

Lary, Banning G., "An Epicaridal Purse String Suture for Closing Coronary Arteriotomy," *The American Surgeon*, Mar. 1967, vol. 33, No. 3, pp. 213-214.

Lary, Banning G., "Coronary Artery Incision and Dilation," *Archives of Surgery*, Dec. 1980, vol. 115, pp. 1478-1480.

Lary, Banning G., "Coronary Artery Resection and Replacement by a Blood Conduit," *Surgery*, Apr. 1969, vol. 65, No. 4, pp. 584-589.

Lary, Banning G., "Effect of Endocardial Incisions on Myocardial Blood Flow," *Archives of Surgery*, Sep. 1963, vol. 87, pp. 424-427.

Lary, B.G., "Experimental Maintenance of Life by Intravenous Oxygen, Preliminary Report," *Clinical Congress of the American College of Surgeons*, San Francisco, Nov. 5-9, 1951, pp. 30-35.

Lary, Banning G., et al., "Experimental Vein Angioplasty of the Circumflex Coronary Artery," *Journal of Surgical Research*, Sep. 1974, vol. 17, No. 3, pp. 210-214.

Lary, Banning G., "Method for Increasing the Diameter of Long Segments of the Coronary Artery," *The American Surgeon*, Jan. 1966, vol. 32, No. 1, pp. 33-35.

Lary, Banning G., et al., "Myocardial Revascularization Experiments Using the Epicardium," *Archives of Surgery*, Jan. 1969, vol. 98, pp. 69-72.

Lary, Banning G., "Onlay Vein Graft for the Correction of Coronary Artery Obstruction," *Surgery*, Apr. 1966, vol. 59, No. 4, pp. 547-551.

Lary, Banning G., "Surgery for Coronary Artery Disease," *Nursing Clinics of North America*, Sep. 1967, vol. 2, No. 3, pp. 537-542.

Lary, Banning G., et al., "The 'Coronary Myocardial Artery' for Coronary Artery Disease," *Diseases of the Chest*, Apr. 1996, vol. 49, No. 4, pp. 412-419.

U.S. Appl. No. 10/821,237, to Gregory S. Kelley, filed Apr. 8, 2004.
U.S. Appl. No. 10/828,572, to Steven A. McAuley et al., filed Apr. 21, 2004.
U.S. Appl. No. 10/828,699, to Karen M. Cheves et al., filed Apr. 21, 2004.
U.S. Appl. No. 10/987,618, to Steven W. Bence et al, filed Nov. 12, 2004.

* cited by examiner

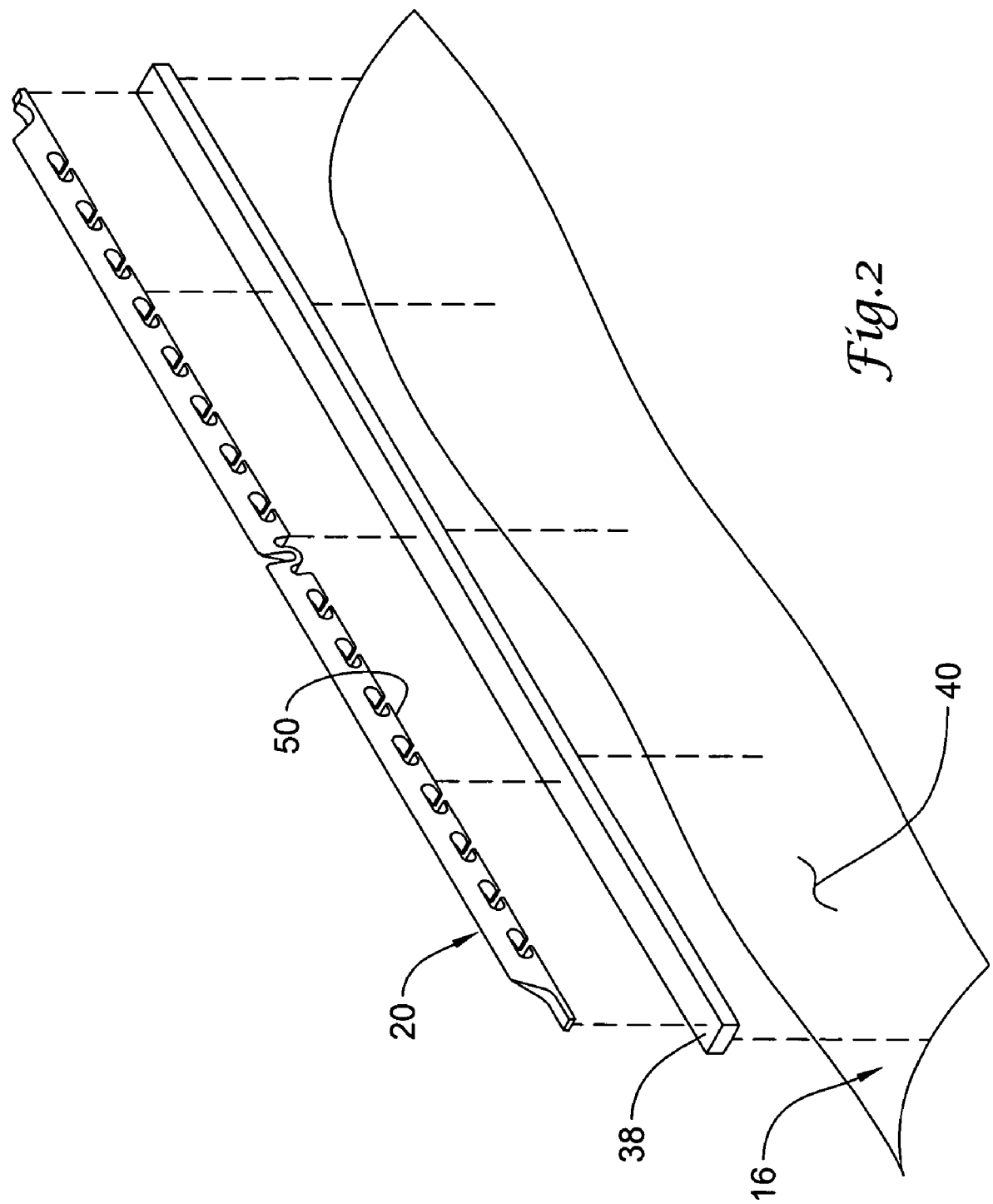

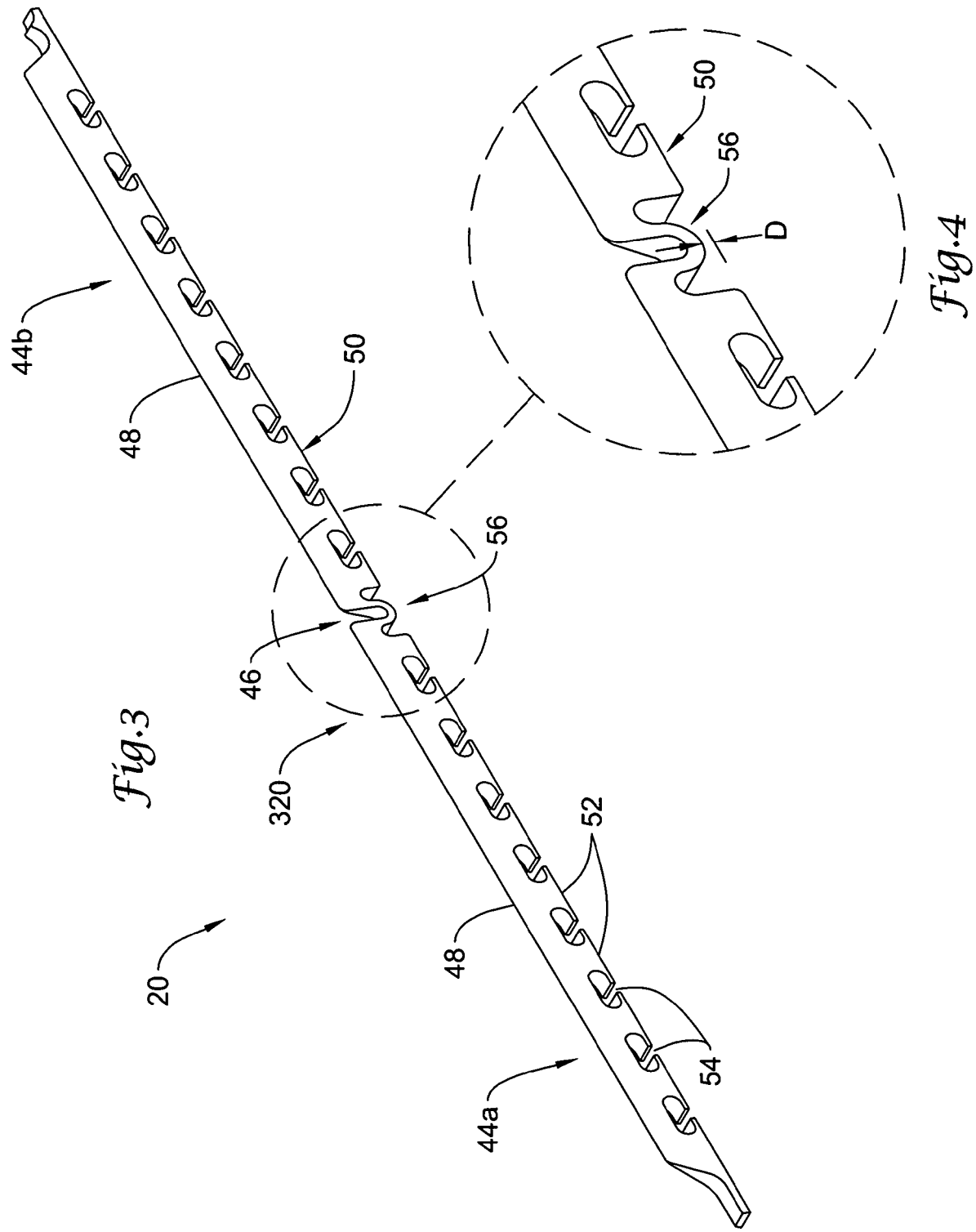

CUTTING BALLOON CATHETER HAVING A SEGMENTED BLADE

FIELD OF THE INVENTION

The present invention pertains to angioplasty and angioplasty balloon catheters. More particularly, the present invention pertains to angioplasty balloon catheters that include one or more cutting blades coupled to the angioplasty balloon.

BACKGROUND

Heart and vascular disease are major problems in the United States and throughout the world. Conditions such as atherosclerosis result in blood vessels becoming blocked or narrowed. This blockage can result in lack of oxygenation of the heart, which has significant consequences, since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire so that the balloon is positioned adjacent a stenotic lesion. The balloon is then inflated, and the restriction of the vessel is opened.

One of the major obstacles in treating coronary artery disease and/or treating blocked blood vessels is re-stenosis. Evidence has shown that cutting the stenosis, for example, with an angioplasty balloon equipped with a cutting blade during treatment, can reduce incidence of re-stenosis. Additionally, cutting the stenosis may reduce trauma at the treatment site and/or may reduce the trauma to adjacent healthy tissue. Cutting blades may also be beneficial additions to angioplasty procedures when the targeted occlusion is hardened or calcified. It is believed typical angioplasty balloons, alone, may not be able to expand certain of these hardened lesions. Thus, angioplasty balloons equipped with cutting edges have been developed to attempt to enhance angioplasty treatments. There is an ongoing need for improved angioplasty devices, including cutting angioplasty balloons, and improved methods of treating intravascular stenoses and occlusions.

BRIEF SUMMARY

The present invention relates to angioplasty balloon catheters. In at least some embodiments, an example balloon catheter may include a catheter shaft having a balloon coupled thereto. One or more cutting members or blades may be coupled to the balloon. The cutting members may include a first section, a second section, and a bridge section disposed between the first and second sections. The bridge section is designed to yield, fracture or separate from the first section, second section, or both when the catheter is disposed within the body. These and other features are described in more detail below.

BRIEF DESCRIPTION OF THE DRAWINGS

FIG. 2 is a partial perspective view of a representative cutting member and a joining member for connecting the cutting member to a balloon;

FIG. 3 is a perspective view of the cutting member of FIG. 2;

FIG. 4 is an enlarged perspective view of a bridge portion included in the cutting member shown in FIG. 3;

DETAILED DESCRIPTION

Figure 1:
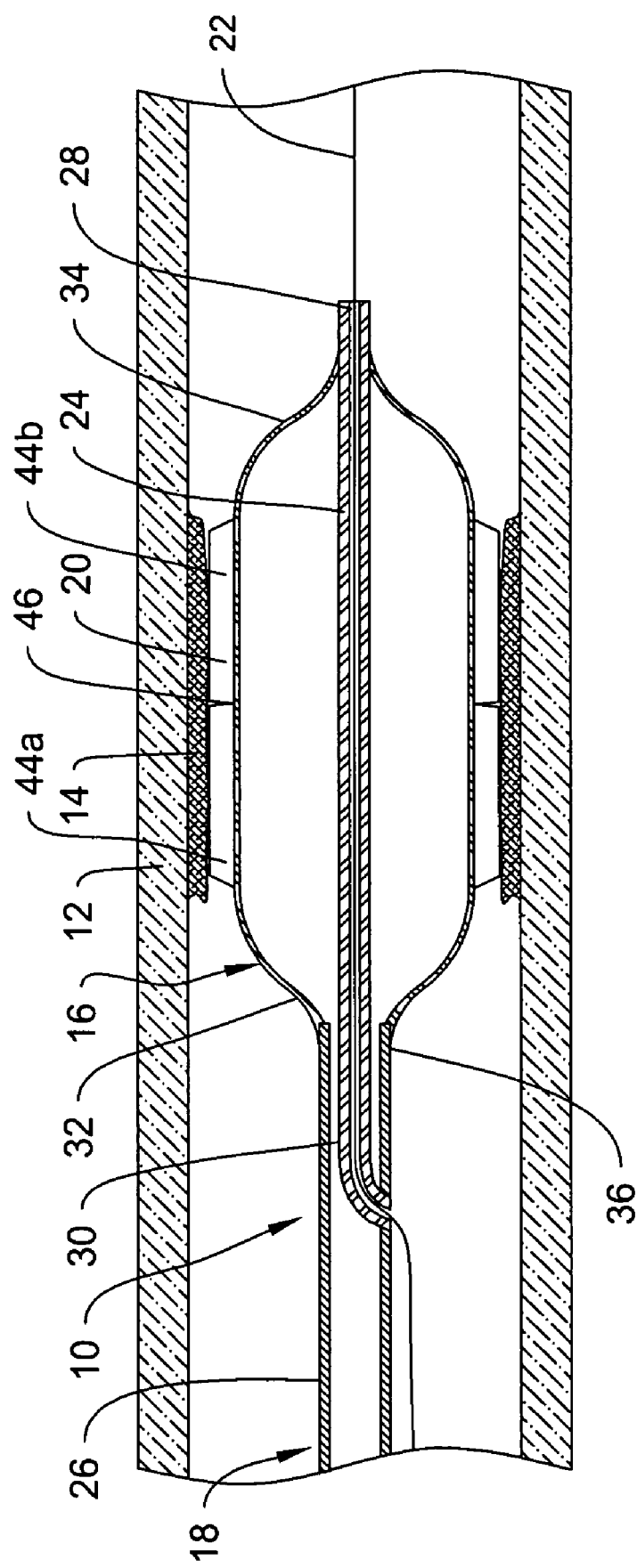
FIG. 1 is a partial cross-sectional side view of an example cutting balloon catheter disposed in a blood vessel.

The following description should be read with reference to the drawings wherein like reference numerals indicate like elements throughout the several views. The detailed description and drawings illustrate example embodiments of the claimed invention.

FIG. 1 is a partial cross-sectional side view of an example catheter 10 disposed in a blood vessel 12 and positioned adjacent an intravascular lesion 14. Catheter 10 may include a balloon 16 coupled to a catheter shaft 18. One or more cutting members or blades 20 may be coupled to balloon 16. In general, catheter 10 may be advanced over a guidewire 22, through the vasculature, to a target area. Balloon 16 can then be inflated to expand lesion 14, and cutting members 20 may cut lesion 14. The target area may be within any suitable peripheral or cardiac vessel lumen location.

Cutting members 20 may vary in number, position, and arrangement about balloon 16. For example, catheter 10 may include one, two, three, four, five, six, or more cutting members 20 that are disposed at any position along balloon 16 and in a regular, irregular, or any other suitable pattern. In general, cutting members 20 may be configured to be have variable flexibility or otherwise vary the flexibility of catheter 10. Increasing the flexibility of cutting members 20 and/or catheter 10 may be desirable, for example, because it may improve the tracking ability and general deliverability of catheter 10 through the often tortuous anatomy. Additionally, increasing the flexibility may allow catheter 10 to be navigable to a larger number of intravascular locations, including some that may not be readily reachable by other, less flexible, cutting balloon catheters. In general, the enhanced flexibility is the result of a structural feature of cutting members 20 or a structural modification to cutting members 20. For example, cutting members 20 may include a first section 44a, a second section 44b, and a bridge or bridge section 46 disposed between first section 44a and second section 44b. Bridge 46 may be configured to separate from first section 44a, second section 44b, or both. Separation of bridge 46 from sections 44a/b can increase the flexibility of cutting member 20 and/or the overall flexibility of catheter 10. Some further discussion of this and other examples, features, and modifications are described in more detail below.

Cutting members 20 may be made from any suitable material such as a metal, metal alloy, polymer, metal-polymer composite, and the like, or any other suitable material. For example, cutting members 20 may be made from stainless steel such as 304V, 304L, or 316L stainless steel. In other embodiments, cutting member 20 can be made from a glass/KEVLAR® complex material such as ARA-MAT®, which is commercially available. Some examples of other suitable materials are listed below in relation to balloon 16 and shaft 18.

Balloon 16 may be made from typical angioplasty balloon materials including polymers such as polyethylene terephthalate (PET), polyetherimid (PEI), polyethylene (PE), etc. Some other examples of suitable polymers, including lubricious polymers, may include polytetrafluoroethylene (PTFE), ethylene tetrafluoroethylene (ETFE), fluorinated ethylene propylene (FEP), polyoxymethylene (POM), polybutylene terephthalate (PBT), polyether block ester, polyurethane, polypropylene (PP), polyvinylchloride (PVC), polyether-ester (for example, a polyether-ester elastomer such as ARNITEL® available from DSM Engineering Plastics), polyester (for example, a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example, available under the trade name PEBAX®), silicones, Marlex high-density polyethylene, Marlex low-density polyethylene, linear low density polyethylene (for example, REXELL®), polyetheretherketone (PEEK), polyimide (PI), polyphenylene sulfide (PPS), polyphenylene oxide (PPO), polysulfone, nylon, perfluoro (propyl vinyl ether) (PFA), other suitable materials, or mixtures, combinations, copolymers thereof, polymer/metal composites, and the like. In some embodiments, it may be desirable to use high modulus or generally stiffer materials so as to reduce balloon elongation. The above list of materials includes some examples of higher modulus materials. Some other examples of stiffer materials include polymers blended with liquid crystal polymer (LCP) as well as the materials listed above. For example, the mixture can contain up to about 5% LCP.

Balloon 16 may be configured so that it includes one or more "wings" or wing-shaped regions when balloon 16 is deflated. These wings may appear as a plurality of alternating inward and outward radial deflections in balloon 16 when balloon 16 is deflated. These wings may be desirable for a number of reasons. For example, by including balloon 16 with wings, balloon 16 may have more predictable and consistent re-folding characteristics. Additionally, the wings may be configured so that cutting members 20 can be positioned at the inward-most positions of the deflated balloon 16. This arrangement allows cutting members 20 to be positioned more closely to shaft 18 when balloon 16 is deflated. Accordingly, cutting members 20 can be moved away from the vessel walls where they might otherwise result in contact and, possibly, damage to healthy tissue during movement of catheter 10 within a body lumen. Additionally, alternating the wings and cutting members 20 as well as positioning cutting members 20 relatively close to shaft 18 may allow the wings to fold over and cover cutting members 20 when balloon 16 is deflated. Again, this feature may reduce the exposure of cutting members 20 to the blood vessel.

Shaft 18 may be a catheter shaft, similar to typical catheter shafts. For example, shaft 18 may include an inner tubular member 24 and outer tubular member 26. Tubular members 24/26 may be manufactured from a number of different materials. For example, tubular members 24/26 may be made of metals, metal alloys, polymers, metal-polymer composites or any other suitable materials. Some examples of suitable metals and metal alloys include stainless steel, such as 300 series stainless steel (including 304V, 304L, and 316L); 400 series martensitic stainless steel; tool steel; nickel-titanium alloy such as linear-elastic or super-elastic Nitinol, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 625, or the like; or other suitable material. Some examples of suitable polymers include those described above in relation to balloon 16. Of course, any other polymer or other suitable material including ceramics may be used without departing from the spirit of the invention. The materials used to manufacture inner tubular member 24 may be the same as or be different from the materials used to manufacture outer tubular member 26. Those materials listed herein may also be used for manufacturing other components of catheter 10 including cutting members 20.

Tubular members 24/26 may be arranged in any appropriate way. For example, in some embodiments, inner tubular member 24 can be disposed coaxially within outer tubular member 26. According to these embodiments, inner and outer tubular members 24/26 may or may not be secured to one another along the general longitudinal axis of shaft 18. Alternatively, inner tubular member 24 may follow the inner wall or otherwise be disposed adjacent the inner wall of outer tubular member 26. Again, inner and outer tubular members 24/26 may or may not be secured to one another. For example, inner and outer tubular members 24/26 may be bonded, welded (including tack welding or any other welding technique), or otherwise secured at a bond point. In some embodiments, the bond point may be generally disposed near the distal end of shaft 18. However, one or more bond points may be disposed at any position along shaft 18. The bond may desirably impact, for example, the stability and the ability of tubular members 24/26 to maintain their position relative to one another. In still other embodiments, inner and outer tubular member 24/26 may be adjacent to and substantially parallel to one another so that they are non-overlapping. In these embodiments, shaft 18 may include an outer sheath that is disposed over tubular members 24/26.

Inner tubular member 24 may include an inner lumen 28. In at least some embodiments, inner lumen 28 is a guidewire lumen. Accordingly, catheter 10 can be advanced over guidewire 22 to the desired location. The guidewire lumen may extend along essentially the entire length of catheter shaft 18 so that catheter 10 resembles a traditional "over-the-wire" catheter. Alternatively, the guidewire lumen may extend along only a portion of shaft 18 so that catheter 10 resembles a "single-operator-exchange" or "rapid-exchange" catheter. Regardless of which type of catheter is contemplated, catheter 10 may be configured so that balloon 16 is disposed over at least a region of inner lumen 28. In at least some of these embodiments, inner lumen 28 (i.e., the portion of inner lumen 28 that balloon 16 is disposed over) may be substantially coaxial with balloon 16.

Shaft 18 may also include an inflation lumen 30 that may be used, for example, to transport inflation media to and from balloon 16. The location and position of inflation lumen 30 may vary, depending on the configuration of tubular members 24/26. For example, when outer tubular member 26 is disposed over inner tubular member 24, inflation lumen 30 may be defined within the space between tubular members 24/26. Moreover, depending on the position of inner tubular member 24 within outer tubular member 26, the shape of lumen 30 (i.e., the shape adjacent shaft 18) may vary. For example, if inner tubular member 24 is attached to or disposed adjacent to the inside surface of outer tubular member 26, then inflation lumen 30 may be generally half-moon in shape; whereas, if inner tubular member 24 is generally coaxial with outer tubular member 26, then inflation lumen 30 may be generally ring-shaped or annular in shape. It can be appreciated that if outer tubular member 26 is disposed alongside inner tubular member 24, then lumen 30 may be the lumen of outer tubular member 26 or it may be the space defined between the outer surface of tubular members 24/26 and the outer sheath disposed thereover.

Balloon 16 may be coupled to catheter shaft 18 in any of a number of suitable ways. For example, balloon 16 may be adhesively or thermally bonded to shaft 18. In some embodiments, a proximal waist 32 of balloon 16 may be bonded to shaft 18, for example, at outer tubular member 26, and a distal waist 34 may be bonded to shaft 18, for example, at inner tubular member 24. The exact bonding positions, however, may vary. It can be appreciated that a section of proximal waist 32 may not have sections 36 extending therefrom in order for suitable bonding between balloon 16 and outer tubular member 30.

In addition to some of the structures described above, shaft 18 may also include a number of other structural elements, including those typically associated with catheter shafts. For example, shaft 18 may include a radiopaque marker coupled thereto that may aid a user in determining the location of catheter 10 within the vasculature. In addition, catheter 10 may include a folding spring (not shown) coupled to balloon 16, for example, adjacent proximal waist 32, which may further help in balloon folding and refolding. A description of a suitable folding spring can be found in U.S. Pat. No. 6,425,882, the disclosure of which is incorporated herein by reference.

An exploded view illustrating the attachment of cutting members 20 to balloon 16 is shown in FIG. 2. Here it can be seen that a joining member or polymeric strip 38 may be coupled to cutting member 20 and to balloon 16. Joining member 38 may be formed from a generally flexible or soft material that allows the interface between cutting member 20 and balloon 16 to be somewhat elastic or pliable. For example, joining member 38 may be manufactured from a low durometer polyurethane or any other suitable material (including any of the polymers and other materials disclosed herein). Accordingly, cutting member 20 may be securely coupled to balloon 16 while still being able to move laterally about eight degrees or less. In addition, different portions of cutting member 20 may be able to bend or flex, while other portions remain essentially unchanged.

In at least some embodiments, joining member 38 can be attached to and disposed between cutting member 20 and balloon 16. For example, joining member 38 can be attached to an outer surface 40 of balloon 16 and to a base 50 of the cutting member 20. The attachment of joining member 38 with cutting member 20 and balloon 16 may be achieved in any appropriate manner, such as by adhesive bonding, casting, thermal bonding, mechanically connecting, welding, brazing, and the like, or in any other suitable way. The attachment means need not be the same for the attachment between cutting member 20 and joining member 38 as the means used to attach balloon 16 and joining member 38.

A more detailed view of cutting member 20 is shown in FIG. 3. Here, first section 44a, second section 44b, and bridge 46 can be more clearly seen. In at least some embodiments, bridge 46 may be defined by a downward deflection or slot that is formed in the cutting surface 48 of cutting member 20. However, this particular example is not intended to be limiting, because bridge 46 can be defined in a number of alternative manners. For example, bridge 46 may comprise an exogenous connector that is connected to both first section 44a and second section 44b in order to connect sections 44a/44b. Some other examples are shown in later figures and described below.

Some of the other features of cutting member 20 can also be seen in FIG. 3. For example, cutting member 20 may include a cutting surface 48 and base 50. Moreover, cutting member 20 may also include a series of alternating tabs 52 and holes or openings 54 that are disposed along the base 50 of cutting member 20. Tabs 52 and openings 54 may be formed in any suitable manner, such as with a wire electric discharge milling technique or any other suitable methodology. Tabs 52 and openings 54 may have a number of functions. For example, openings 54 (or, more precisely, the portions of cutting member 20 adjacent openings 54) may provide a location for an adhesive (e.g., polyurethane or any other suitable material) or polymer strip 38 to flow into so as to improve the bonding of cutting member 20 with balloon 16. The bonding media (e.g., polymeric strip 38) may encapsulate the base 50 of cutting member 20 and, thus, may interlock with cutting member 20 so as to improve the bonding between balloon 16 and cutting member 20. This feature is better seen in FIGS. 5 and 6.

In some embodiments, tabs 52 and openings 54 may desirably impact the flexibility of cutting member 20. Additionally, the shape of tabs 52 and opening 54 may vary. For example, tabs 52 may have a shape similar to an inverted T (when viewed from the side) or otherwise have a splayed pillar-like shape, and openings 54 may be somewhat rounded or oval. It can be appreciated, however, that tabs 52 and openings 54 are not intended to be limited to these or any other particular shape. Moreover, the size and number of tabs 52 and openings 54 may also vary, typically in relation to the length of cutting member 20. For example, openings 54 may have a height in the range of about 0.002 to about 0.010 inches and a width in the range of about 0.007 to about 0.015 inches.

As described above, bridge 46 may be defined by a downward deflection in cutting surface 48 of cutting member 20. In addition to this, the bottom 56 of bridge 46 may also be spatially altered. For example, FIG. 4 illustrates that the bottom 56 of bridge 46 may be raised a distance D relative to the base 50 of cutting member 20. Distance D may be about 0.0001 inches to about 0.010 inches. This feature may be desirable, for example, because it raises bridge 46 up from balloon 16 (when cutting member 20 is coupled to balloon 16) so that bridge 46 is spatially separated from balloon 16 when bridge 46 separates from first section 44a, second section 44b, or both.

Figure 5:
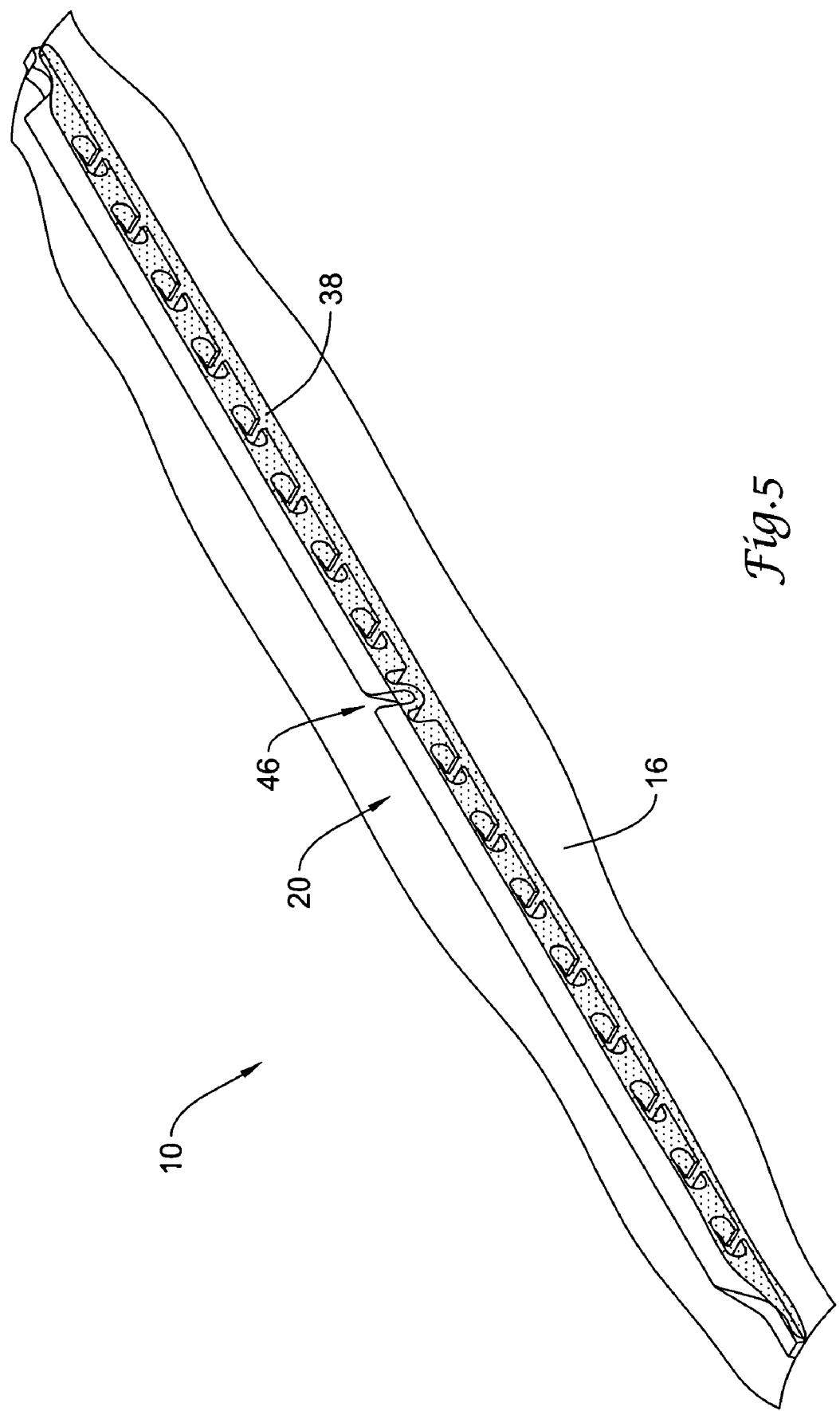
FIG. 5 is a cutaway perspective view of a portion of the cutting member shown attached to a balloon.
Figure 6:
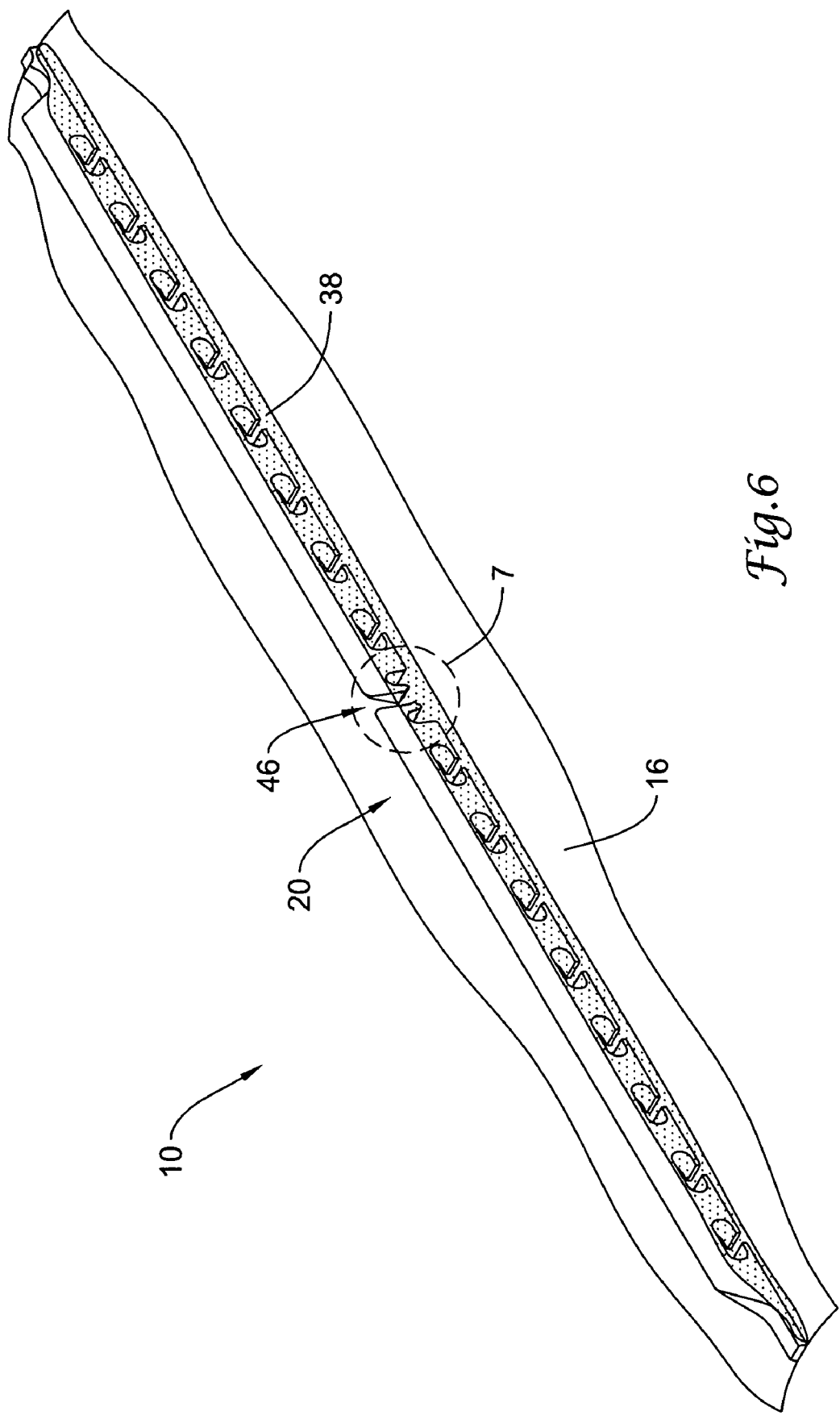
FIG. 6 is a cutaway perspective view of a portion of the cutting member shown attached to a balloon where the bridge is separated from a first section and a second section of the cutting member.

Prior to inserting catheter 10 into the body of a patient, bridge 46 may be connected with both first section 44a and 44b, as shown in FIG. 5. This feature allows cutting member 20 to be longitudinally continuous so as to provide a desirable amount of pushability to catheter 10 when, for example, advancing catheter 10 through the vasculature. Some interventions, however, will require that catheter 10 pass through a bend in the vasculature. In some instances, the bend may be significant so that only devices having a certain amount of flexibility can be easily navigated through the bend. Catheter 10 is configured to be adaptable to changes in the vasculature by being able to vary its flexibility. This variability allows catheter 10 to be easily navigated through tortuous sections of the vasculature. Varying the flexibility of catheter 10 may be accomplished by the inclusion of bridge 46. For example, bridge 46 may be configured to fracture or separate from first section 44a, second section 44b, or both, as shown in FIG. 6. Alternatively, the bridge can include a polymer that is soluble in the environment of use, which in turn weakens the bridge, resulting in yielding in response to the vascular curvature. Accordingly, when catheter 10 encounters a sufficient bend in the vasculature, bridge 46 can separate from first section 44a, second section 44b, or both, thereby increasing the flexibility of cutting member 20 and catheter 10. This increase in flexibility allows catheter 10 to be navigated through the bend in the vasculature and, ultimately, to the final target area. Therefore, catheter 10 is adaptable to varying vasculature conditions and possesses the desired amount of pushability and flexibility when needed for the particular conditions encountered.

Figure 7:
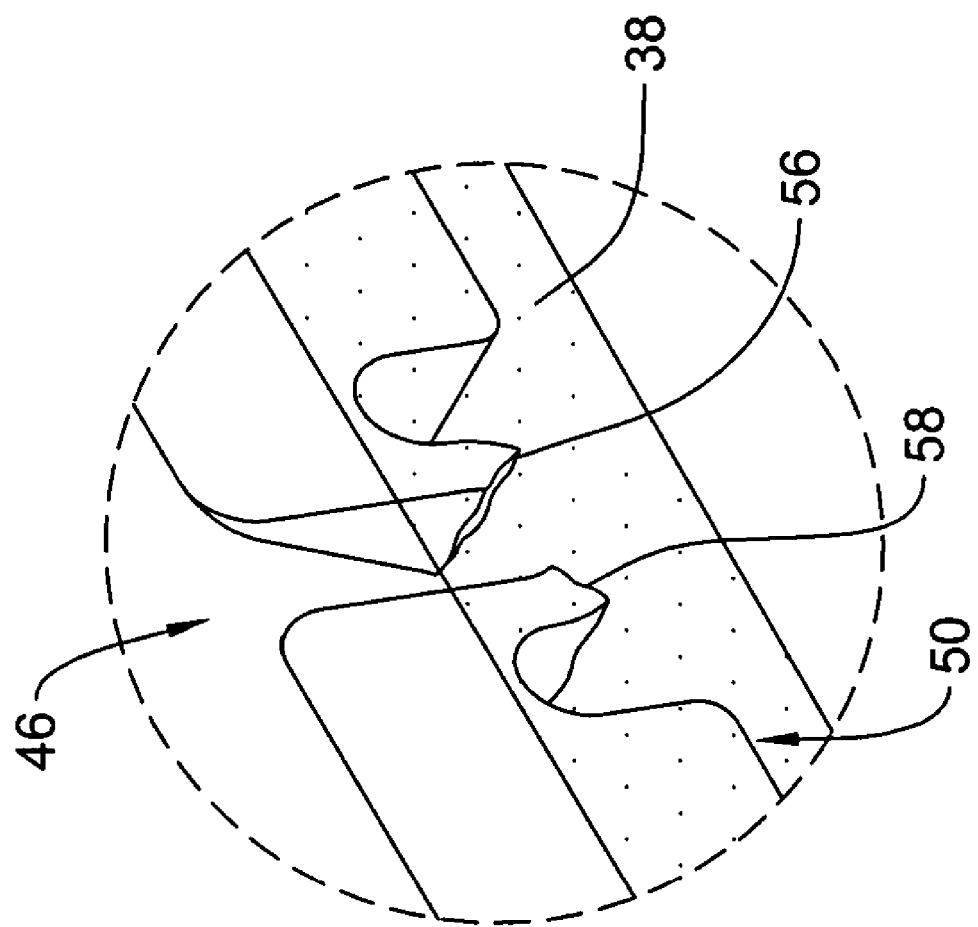
FIG. 7 is an enlarged view of the bridge in FIG. 6 as separated from the first section and the second section of the cutting member.

The separation of bridge 46 from first section 44a and second section 44b is shown in FIGS. 6 and 7. Although bridge 46 is shown in FIGS. 6 and 7 as being separated from both first section 44a and second section 44b, this is not intended to be limiting as bridge 46 may separate from only one of sections 44a/b. In at least some embodiments, bridge 46 is configured to separate from first section 44a, second section 44b, or both after catheter 10 is inserted into the body (e.g., the vasculature) of a patient. For example, bridge 46 may separate when catheter 10 encounters a bend in the vasculature as described above.

Turning now to FIG. 7, it can be seen how the design of bridge 46 allows the separation to be isolated at the bottom 56 of bridge 46 and, thus, the bottom or base 50 of cutting member 20. Therefore, polymer strip 38 at the base 50 of cutting member 20 can surround the separated segments 58 of bridge 46 and shield balloon 16, other portions of the catheter 10, and surrounding tissue from unintentional damage that might otherwise occur if not shielded. The raising of the bottom 56 of bridge 46 can also contribute to this shielding effect by raising bottom 56 away from balloon 16.

Figure 8:
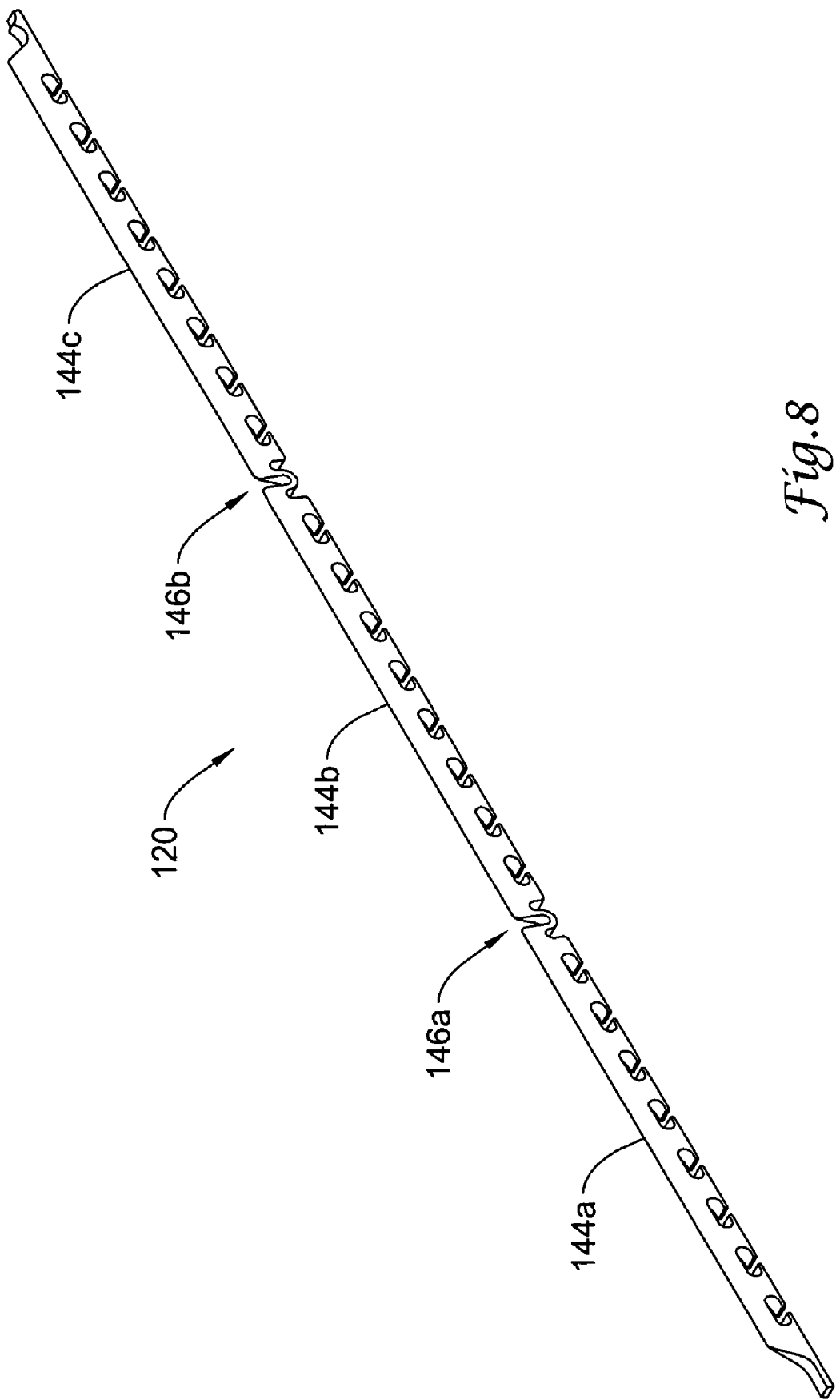
FIG. 8 is a perspective view of another example cutting member.

It can be appreciated that the length of cutting member 20, and the number and position of bridge 46 may vary. For example, the length of cutting member 20 may range from about 4 millimeters to about 20 millimeter or so. Generally, as the length of cutting member 20 increases, the number of sections (e.g., sections 44a/b) and bridges (e.g., bridge 46) that can be included also increases. Accordingly, relatively short or moderate cutting members (e.g., about 4-14 millimeters) may include one bridge similar to bridge 46. Longer cutting members (e.g., about 12 millimeters or longer) may include more than one bridge. For example, FIG. 8 illustrates cutting member 120 that has two bridges 146a/b. Bridge 146a is disposed between first section 144a and second section 144b. Bridge 146b is disposed between second section 144b and a third section 144c. Of course, a number of additional embodiments of cutting members are contemplated that have a variety of lengths and a various numbers of bridges and sections.

Figure 9:
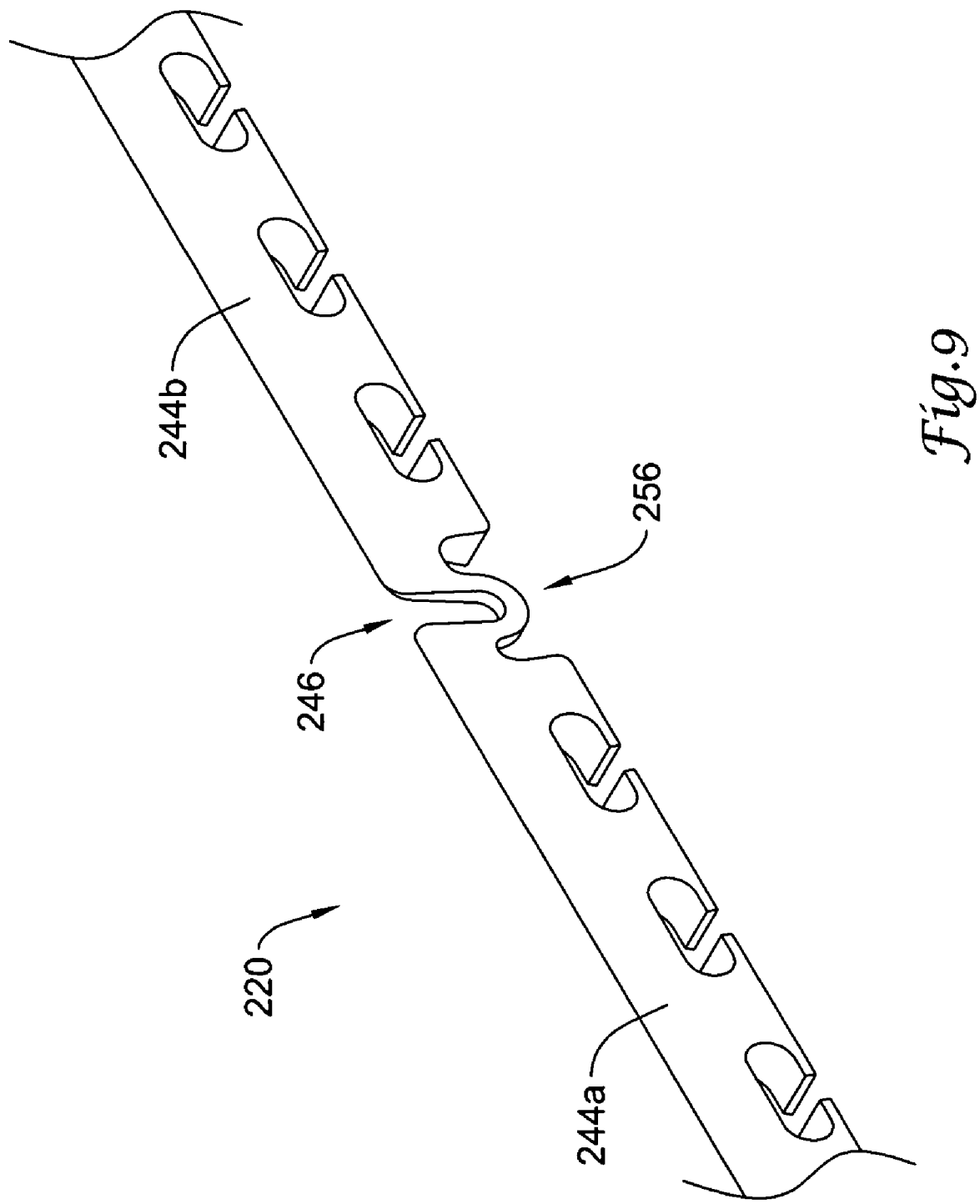
FIG. 9 is a perspective view of another example cutting member.
Figure 10:
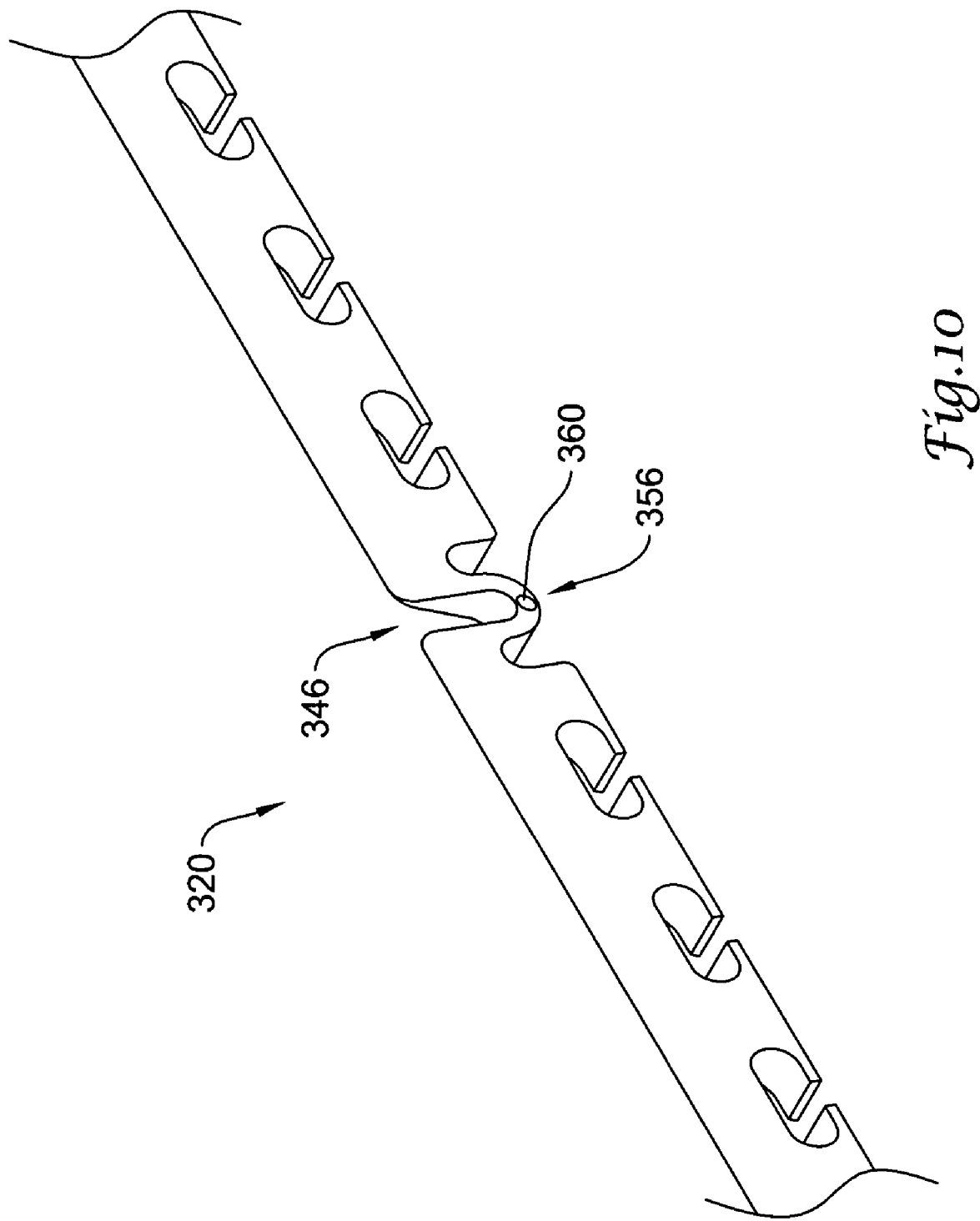
FIG. 10 is a perspective view of another example cutting member.
Figure 11:
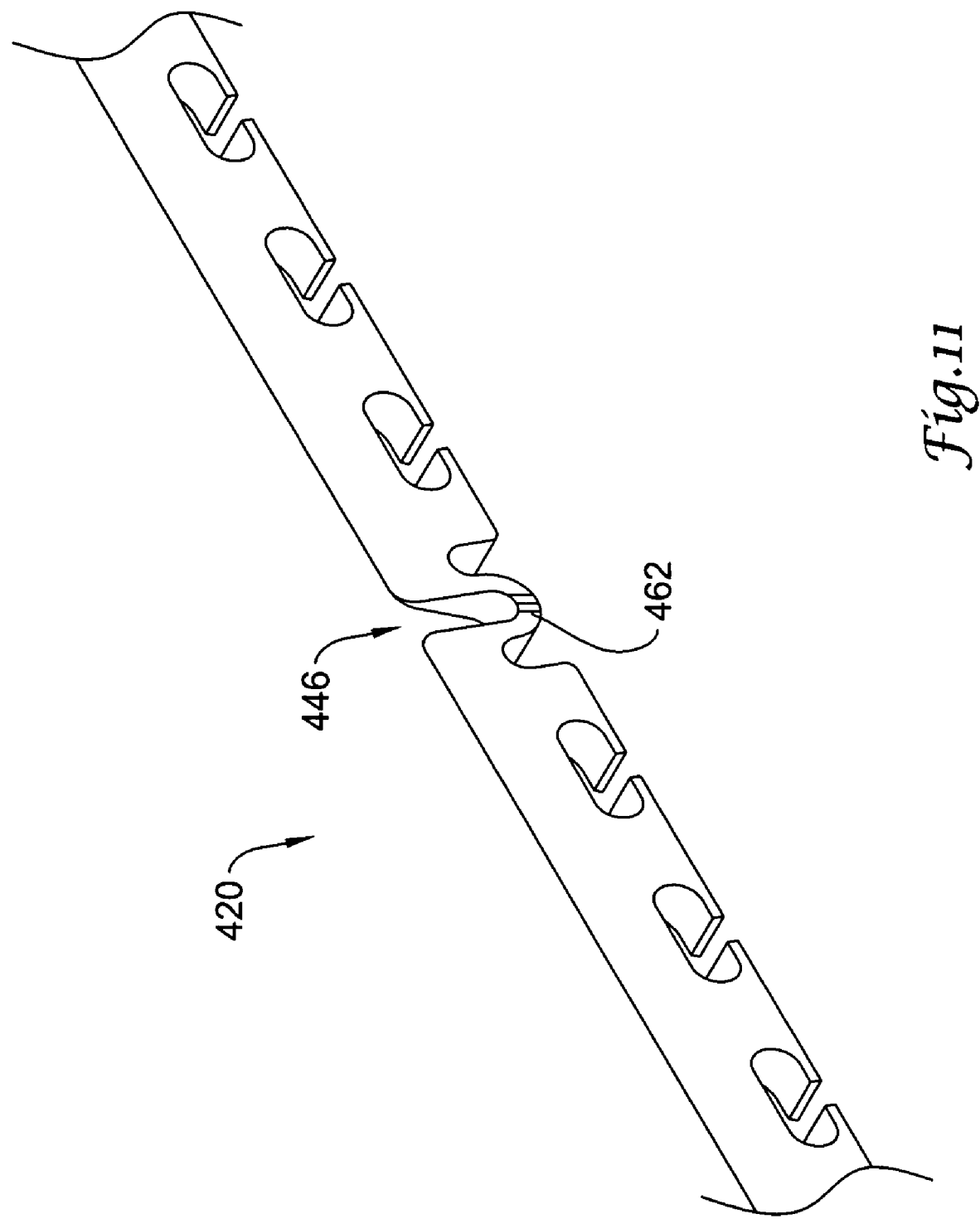
FIG. 11 is a perspective view of another example cutting member.
Figure 12:
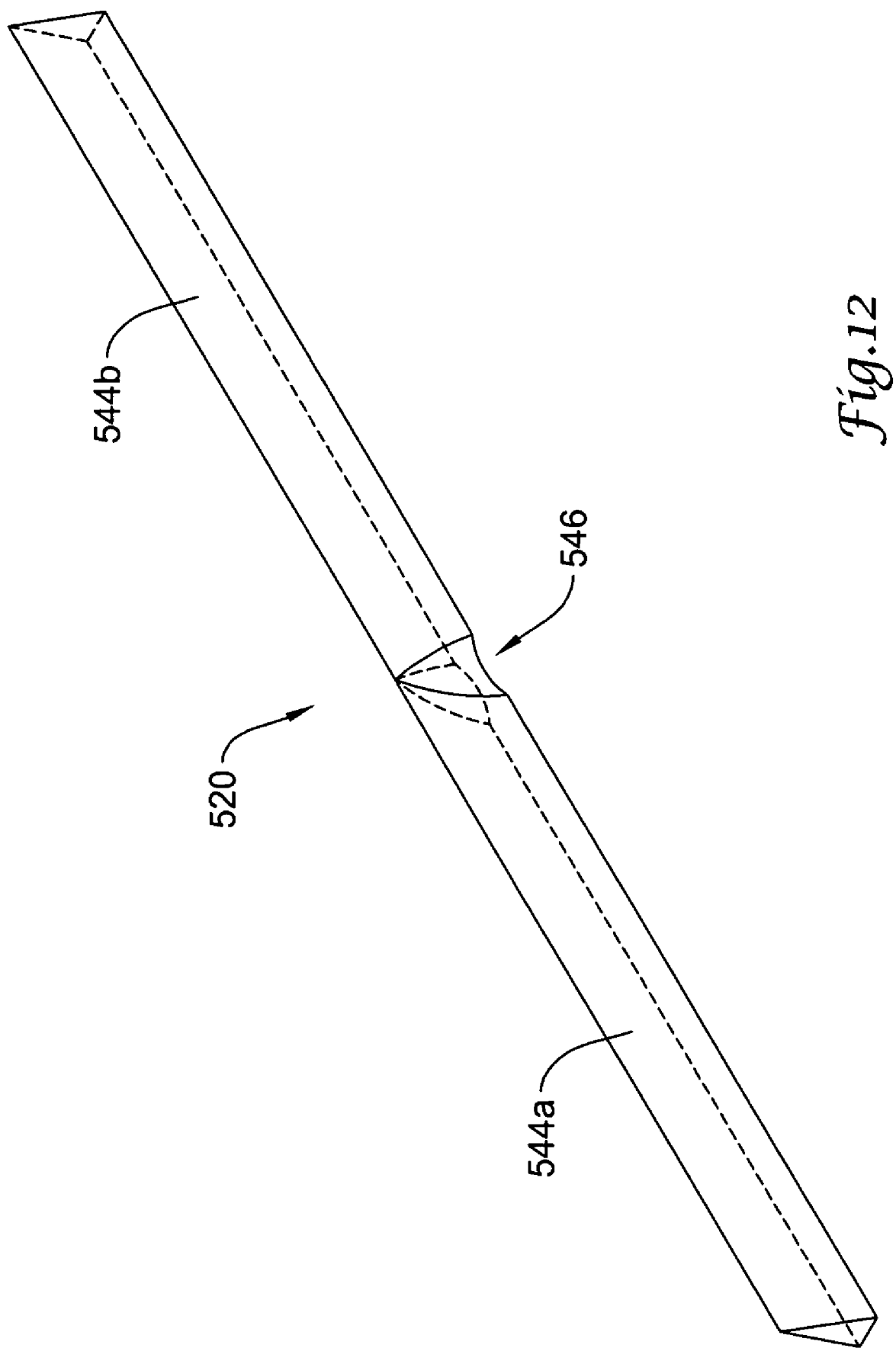
FIG. 12 is a perspective view of another example cutting member.

FIGS. 9-12 illustrate alternative example cutting members for use with any suitable cutting balloon catheter. For example, FIG. 9 illustrates cutting member 220 (which is similar to cutting member 20) that has a thinned base or bottom 256. Although this may be somewhat difficult to see in FIG. 9 alone, the thinning of base 256 can be more easily visualized by comparing the thickness of base 256 in FIG. 9 with the thickness of base 356 in FIG. 10. The thinning feature may enhance the ability of cutting member 220 to fracture or separate from sections 244a/b, which may be desirable for some interventions. The example cutting member 320 depicted in FIG. 10 has a hole or opening 360 defined in bridge 346. Hole 360 may similarly enhance the ability of cutting member 220 to separate. Likewise, FIG. 11 illustrates cutting member 420 that has one or more etches formed in bridge 446 that can enhance the ability of cutting member 420 to separate. Finally, FIG. 12 illustrates another example cutting member 520 where bridge 546 is defined by a general thinning of cutting member 520 between sections 544a/b. Thinned bridge 546 can be formed with a wire electric discharge method or with other suitable methods such as grinding, machining, and the like.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A medical device, comprising:
   an elongate shaft having a distal end region;
   a balloon coupled to the distal end region;
   a cutting member coupled to the balloon, the cutting member having a cutting surface, a base, a first segment, a second segment, and a bridge segment extending between the first segment and the second segment, wherein the bridge segment yields when flexed beyond a selected curvature during use;
   further comprising a joining member disposed adjacent the base of the cutting member and coupled to the balloon;
   wherein the joining member encapsulates the bridge segment; and
   wherein the bridge segment is configured to separate from the first segment, the second segment, or both during use of the medical device.

2. The medical device of claim 1, wherein the bridge segment remains encapsulated in the joining member when the bridge is separated from the first segment, the second segment, or both.

3. A cutting balloon catheter, comprising:
   an elongate catheter shaft;
   a balloon coupled to the catheter shaft;
   a joining member coupled to the balloon; and
   a cutting member coupled to the joining member, the cutting member including a cutting surface extending from a base having a first section and a second section with a bridge disposed therebetween, wherein the bridge selectively yields in response to curvature of the vasculature during use;
   wherein the joining member encapsulates the bridge; and
   wherein the bridge is configured to separate from the first section, the second section, or both during use of the cutting balloon.

4. The cutting balloon of claim 3, wherein the bridge remains encapsulated in the joining member when the bridge is separated from the first section, the second section, or both.

5. A method of using a cutting balloon catheter, comprising the steps of:
  providing a cutting balloon catheter, the cutting balloon catheter including an elongate catheter shaft, a balloon coupled to shaft, and one or more cutting members coupled to the balloon, the cutting members each including a cutting surface extending from a base including a first section and a second section with a bridge disposed between the first section and the second section that yields when flexed beyond a selected curvature;
  advancing the cutting balloon catheter through a blood vessel to a position adjacent an area of interest;
  inflating the balloon, whereby the balloon and the cutting members engage the area of interest;
  deflating the balloon;
  withdrawing the cutting balloon catheter from the blood vessel; and
  wherein the step of advancing the cutting balloon catheter through a blood vessel to a position adjacent an area of interest includes separating one or more of the bridges from the corresponding first section, second section, or both.

6. The method of claim 5, wherein the bridges remains encapsulated in the polymeric strip when one or more of the bridges are separated from the corresponding first section, second section, or both.

* * * * *